US012734210B2

(12) United States Patent
Chung et al.

(10) Patent No.: US 12,734,210 B2
(45) Date of Patent: Sep. 15, 2026

(54) PEPTIDE HAVING HAIR LOSS PREVENTION OR HAIR GROWTH PROMOTION ACTIVITY AND USE THEREOF

(71) Applicant: CAREGEN CO., LTD., Gyeonggi-do (KR)

(72) Inventors: Yong Ji Chung, Gyeonggi-do (KR); Eun Mi Kim, Gyeonggi-do (KR); Eung Ji Lee, Gyeonggi-do (KR); Min Woong Kim, Gyeonggi-do (KR); Hana Gil, Gyeonggi-do (KR)

(73) Assignee: CAREGEN CO., LTD., Gyeonggi-Do (KR)

( * ) Notice: Subject to any disclaimer, the term of this patent is extended or adjusted under 35 U.S.C. 154(b) by 338 days.

(21) Appl. No.: 18/695,562

(22) PCT Filed: Sep. 28, 2022

(86) PCT No.: PCT/KR2022/014520

§ 371 (c)(1),
(2) Date: Mar. 26, 2024

(87) PCT Pub. No.: WO2023/055053

PCT Pub. Date: Apr. 6, 2023

(65) Prior Publication Data

US 2025/0127844 A1 Apr. 24, 2025

(30) Foreign Application Priority Data

Oct. 1, 2021 (KR) ........................ 10-2021-0130817

(51) Int. Cl.
*A61K 38/08* (2019.01)
*A61P 17/14* (2006.01)
*C07K 7/06* (2006.01)

(52) U.S. Cl.
CPC .............. *A61K 38/08* (2013.01); *A61P 17/14* (2018.01); *C07K 7/06* (2013.01)

(58) Field of Classification Search
None
See application file for complete search history.

(56) References Cited

U.S. PATENT DOCUMENTS

| | | | |
|---|---|---|---|
| 6,069,129 | A | 5/2000 | Sandberg |
| 7,115,398 | B2 | 10/2006 | Chen |
| 8,460,647 | B2 | 6/2013 | Gaffen |
| 9,416,168 | B2 | 8/2016 | Aharoni |
| 2014/0309157 | A1 | 10/2014 | Chung |
| 2016/0074470 | A1 | 3/2016 | Chueh |
| 2016/0272679 | A1 | 9/2016 | Chung |
| 2017/0049847 | A1 | 2/2017 | Chung |
| 2017/0080046 | A1 | 3/2017 | Poigny |
| 2017/0267721 | A1 | 9/2017 | Chung |
| 2019/0040100 | A1 | 2/2019 | Chung |
| 2019/0046427 | A1 | 2/2019 | Chung |
| 2020/0087374 | A1 | 3/2020 | Wensvoort |
| 2020/0317741 | A1 | 10/2020 | Kim |
| 2022/0009988 | A1 | 1/2022 | Wensvoort |
| 2022/0259263 | A1 | 8/2022 | Chung |
| 2022/0265538 | A1 | 8/2022 | Chung |
| 2024/0027431 | A1 | 1/2024 | Wensvoort |

FOREIGN PATENT DOCUMENTS

| | | | |
|---|---|---|---|
| CN | 108699109 | A | 10/2018 |
| CN | 109970842 | A | 7/2019 |
| CN | 112041329 | A | 12/2020 |
| EP | 2740741 | A1 | 6/2014 |
| JP | 2014-521685 | A | 8/2014 |
| KR | 10-2015-0029888 | A | 3/2015 |
| KR | 10-2016-0069054 | A | 6/2016 |
| KR | 10-2017-0046528 | A | 5/2017 |
| KR | 10-2017-0097830 | A | 8/2017 |
| KR | 10-2018-0019968 | A | 2/2018 |
| KR | 10-2020-0058932 | A | 5/2020 |
| WO | 2018-141969 | A1 | 8/2018 |
| WO | 2021/033830 | A1 | 2/2021 |
| WO | 2021/033832 | A1 | 2/2021 |

OTHER PUBLICATIONS

Uniprot entry J9FQV7 (2012).*
Chinese Office Action issued by the China National Intellectual Property Administration on Jan. 27, 2026 in corresponding CN Patent Application No. 202280066459.4, with English translation.
International Search Report and Written Opinion issued in corresponding International Application No. PCT/KR2022/014520 dated Jan. 6, 2023, pp. 1-10, with English Translation of ISR only.
Ohn, J. et al., "Discovery of a transdermally deliverable pentapeptide for activating AdipoR1 to promote hair growth" EMBO Molecular Medicine (Sep. 2021) pp. 1-14, vol. 13, e13790.
NCBI. Genbank accession No. WP_130606980.1 (Apr. 17, 2020) pp. 1-2.
Baud, S. et al., "Elastin peptides in aging and pathological conditions" Biomolecular Concepts (Feb. 2013) pp. 65-76, vol. 4, No. 1.
Angela Cristina Mora Huertas, "Degradation of skin elastin in ageing and disease: an ex vivo quantitative proteomic approach" Doctoral thesis, Martin-Luther-Universitat Halle-Wittenberg (Sep. 2017) pp. 1-110.
Extended European Search Report issued by the European Patent Office on Mar. 13, 2025 in corresponding EP Patent Application No. 22876825.5.

* cited by examiner

*Primary Examiner* — Fred H Reynolds
(74) *Attorney, Agent, or Firm* — Carter, DeLuca & Farrell LLP

(57) ABSTRACT

The present invention relates to a peptide of a novel sequence that has hair growth promotion and hair loss prevention activity. The peptide has activity that can promote or induce the proliferation or activity of cells related to hair formation, and thus a composition containing the peptide can be usefully used for preventing hair loss or promoting hair growth.

18 Claims, 3 Drawing Sheets

Specification includes a Sequence Listing.

PEPTIDE HAVING HAIR LOSS PREVENTION OR HAIR GROWTH PROMOTION ACTIVITY AND USE THEREOF

CROSS-REFERENCE TO RELATED APPLICATIONS

The present application is a national stage application of International Application No. PCT/KR2022/014520, filed Sep. 28, 2022, which claims priority to and the benefit of Korean Patent Application No. 10-2021-0130817 filed in the Korean Intellectual Property Office on Oct. 1, 2021, all of the foregoing disclosures hereby incorporated by reference in their entirety.

[Sequence Listing]

The application contains a Sequence Listing which has been submitted electronically in.XML format together with the International Application and is hereby incorporated by reference in its entirety. Said.XML copy, created on Sep. 27, 2022 is named "6166PCT-Seq.xml" and is 15,819 bytes in size.

TECHNICAL FIELD

The present invention related to a novel peptide having activity that can improve hair loss or promote hair growth and an use thereof.

BACKGROUND ART

The average number of hairs in the human body is about 100,000 to 150,000, and as cell division and activity of hair follicles stop in the process of repeated growth, degeneration, and resting, existing hairs are pushed out by new growing hairs and fall out naturally. This natural hair loss phenomenon occurs when an average of about 100 hairs fall out per day. Hair loss occurs as a type of disease when a larger amount of hair falls out than the natural hair loss as described above, or when hair does not exist or does not grow in areas where hair should normally exist. Hair loss can occur during the natural aging process, but can also be caused by external environmental factors such as hormonal changes, stress, air pollution, and processed foods.

As hair loss progresses, the dermal papilla present in the hair root becomes smaller, and accordingly, the thickness of the hair growing from the dermal papilla becomes thinner, and the hair cycle of growth, regression, and resting hair also becomes shorter, making the newly growing hair even thinner. As this phenomenon is repeated, the increasingly thinner hair turns into fluff, and the hair cycle gradually becomes shorter, causing the hair to grow less quickly and fall out, resulting in a decrease in the overall number of hairs. In the past, it was considered a phenomenon or disease that mainly occurred in older men, but statistics show that close to half of hair loss patients are young patients in their 20s and 30s, and the number of female patients is also gradually increasing. Since hair loss causes significant changes in the external aspect, the cost of hair loss treatment, such as receiving transplant surgery or taking treatment for hair loss, is gradually increasing among young people who are interested in beauty and appearance.

Nevertheless, research and development of effective treatments for hair loss are still insufficient. Korean Laid-open Patent Publication No. 2020-0058932 discloses a composition for preventing hair loss and improving hair loss containing bellflower extract, etc., and Korean Laid-open Patent Publication No. 2017-0046528 discloses a complex composition for improving hair loss and preventing hair loss containing various herbal medicine extracts. However, there is a problem that unpredictable side effects may occur due to the use of various types of natural products that may contain various ingredients. In particular, treatments that regulate hormones have the disadvantage of causing side effects related to sexual function or not being applicable to women. On the other hand, if a peptide with a hair loss treatment effect among peptides composed of amino acids is developed and used as a hair loss treatment, it has the advantage of being highly biocompatible and having the potential to exhibit similar activity by mimicking the active site of other proteins in the human body. In addition, as a single peptide is used, the mechanism of action is clear compared to extracts containing various ingredients, and after locally suppressing hair loss, it can be easily decomposed and removed by body decomposition proteins. Therefore, unlike existing treatments, there is less concern about side effects. Accordingly, there is an urgent need to develop a peptide agent that can effectively prevent hair loss and promote hair growth with fewer side effects.

PRIOR ART DOCUMENTS

Patent Documents (Patent Document 1) Korean Patent Laid-open Publication No. 2020-0058932

(Patent Document 2) Korean Patent Laid-open Publication No. 2017-0046528

DISCLOSURE

Technical Problem

It is an object of the present invention to provide a peptide that can promote hair growth by having the activity of inducing an increase in the proliferation or activity of cells related to hair formation.

It is another object of the present invention to provide a composition for effectively preventing, treating, improving hair loss, or promoting hair growth using the peptide.

Technical Solution

In order to achieve the above objects, one aspect of the present invention provides a peptide having the activity of preventing hair loss or promoting hair growth, comprising an amino acid sequence of SEQ ID NO: 1.

Another aspect of the present invention provides a composition for preventing hair loss or promoting hair growth, comprising the peptide.

Still another aspect of the present invention provides a pharmaceutical composition for preventing or treating hair loss, comprising the peptide.

Yet another aspect of the present invention provides a cosmetic composition for preventing or improving hair loss, comprising the peptide.

Hereinafter, the present invention will be described in detail.

1. Peptide Having the Activity of Preventing Hair Loss or Promoting Hair Growth and Use Thereof One aspect of the present invention provides a novel peptide that has the activity of preventing hair loss or promoting hair growth.

In the present invention, the term "peptide" refers to a polymer composed of two or more amino acids linked by a peptide bond.

In the present invention, the term "hair loss" means the absence of hair in areas where hair should normally exist, and includes a phenomenon in which the number of hairs decreases compared to the normal state. The hair loss is a concept that includes both non-cicatrical alopecia and cicatrical alopecia depending on whether the hair follicle is destroyed, for example, hereditary androgenetic alopecia, alopecia areata, tinea capitis due to fungal infection, telogen alopecia, trichotillomania, hair loss due to hair growth disorder disease or lupus, folliculitis decalvans, lichen planus pilaris, hair loss due to burns and/or trauma.

The peptide contains the amino acid sequence of SEQ ID NO: 1. The peptide may include a variant peptide having a different sequence due to deletion, insertion, substitution, or a combination thereof of amino acid residues, to the extent that it does not affect the activity of the peptide, or may be in the form of a protein fragment with the same function. Amino acid modifications at the protein and peptide level that do not overall alter activity by including the amino acid sequence of SEQ ID NO: 1 are known in the art. In some cases, it may be modified by phosphorylation, sulfation, acrylation, glycosylation, methylation, farnesylation, etc. Accordingly, the peptide includes not only the amino acid sequence of SEQ ID NO: 1, but also a peptide or a variant thereof having an amino acid sequence substantially identical thereto. The peptide having substantially the same amino acid sequence may be a peptide containing an amino acid sequence having at least 90%, at least 91%, at least 92%, at least 93%, at least 94%, at least 95%, at least 96%, at least 97%, at least 98%, at least 99%, or at least 99.5% homology to the amino acid sequence of SEQ ID NO: 1, but is not limited thereto. Any peptide containing a sequence having at least 90% amino acid sequence homology to the amino acid sequence of SEQ ID NO: 1 and having the same activity is included in the scope of the present invention.

The peptide of the present invention may be composed of 20 or less amino acids that contain the amino acid sequence of SEQ ID NO: 1 and exhibit activity in preventing hair loss or promoting hair growth. Specifically, the peptide may be composed of 20 or less, 18 or less, 15 or less, or 12 amino acids.

In addition, the peptide of the present invention can be obtained by various methods well known in the art. As an example, it can be manufactured using polynucleotide recombination and protein expression systems, in vitro synthesis through chemical synthesis such as peptide synthesis, and cell-free protein synthesis, but is not limited by the manufacturing method.

In addition, to obtain better chemical stability, enhanced pharmacological properties (half-life, absorption, potency, efficacy etc.), altered specificity (e.g. broad spectrum of biological activity), and reduced antigenicity, a protecting group may be attached to the N-terminus or C-terminus of the peptide. For example, the protecting group may be an acetyl group, fluorenyl methoxy carbonyl group, formyl group, palmitoyl group, myristyl group, stearyl group, or polyethylene glycol (PEG), but any component that can modify the peptide, especially improving the stability of the peptide, can be included without limitation. The 'stability' refers not only to in vivo stability, which protects the peptide of the present invention from attack by protein-cleaving enzymes in vivo, but also to storage stability (e.g., storage stability at room temperature).

The peptide of the present invention may promote the proliferation or activity of cells related to hair formation. Specifically, the peptide can have an activity that promotes the proliferation of cells related to hair formation, such as dermal papilla cell, outer root sheath cell, germinal matrix cell, thereby increasing their number, or have an activity that induces hair formation by promoting the activity of the cells.

In addition, the peptide of the present invention may inhibit the expression of a protein related to the occurrence of hair loss in cells related to hair formation. Specifically, it may inhibit the expression of DKK-1 protein (dickkopf-related protein 1) in dermal papilla cells, and may inhibit the expression of DKK-1 protein in dermal papilla cells where the expression of DKK-1 protein is induced by hormones such as DHT (dihydrotestosterone).

Since the peptide of the present invention has the above activities, it can be usefully used to prevent hair loss or promote hair growth.

Accordingly, another aspect of the present invention provides a composition for preventing hair loss or promoting hair growth, comprising the peptide.

The peptide may be included in the composition at a concentration of 0.01 μM to 100 μM. Specifically, the peptide may be included at a concentration of 0.01 μM to 100 μM, 0.05 μM to 80 μM, 0.1 μM to 60 μM, or 0.5 μM to 50 μM, but is not limited thereto. When the concentration of the peptide included in the composition of the present invention is within the above range, there is an advantage that the activity of the peptide sufficiently prevents hair loss and/or promotes hair growth, while showing no toxicity to living organisms or their cells.

The composition may induce hair formation by promoting the activity of one or more cells selected from the group consisting of dermal papilla cells, outer root sheath cells, and germinal matrix cells.

The composition may induce one or more phosphorylation selected from the group consisting of AKT and ERK in dermal papilla cells. Specifically, the composition can increase the amount of p-AKT and/or p-ERK in dermal papilla cells, thereby activating signaling pathways related to the proliferation of dermal papilla cells.

The composition may induce the activation of β-catenin in dermal papilla cells. Specifically, the composition can activate β-catenin in dermal papilla cells and induce its movement to the nucleus, thereby promoting or inducing cell proliferation and/or differentiation of dermal papilla cells.

The composition may promote the expression of one or more selected from the group consisting of LEF-1, c-Myc and cyclin D1 in dermal papilla cells. Specifically, the composition may promote or induce cell proliferation and/or differentiation in dermal papilla cells, thereby promoting the expression of LEF-1, c-Myc and/or cyclin D1.

In a specific embodiment of the present invention, the composition containing the peptide of the present invention was treated at different concentrations to human hair follicle dermal papilla cell (HHFDPC) and the absorbance was measured. As a result, the absorbance was measured to be greater than that of the control group, confirming the effect of promoting and inducing the proliferation of HHFDPC. In addition, in the HHFDPC, p-AKT and p-ERK, which are factors related to proliferation or activation, were increased, and β-catenin was activated, resulting in increased migration to the nucleus and corresponding increase in the expression of LEF-1, c-Myc and cyclin D1. Therefore, it was confirmed that the peptide of the present invention and the composition comprising the same are excellent in promoting hair growth or preventing hair loss by promoting and inducing the proliferation and activation of dermal papilla cells, which are cells forming hair follicles.

The composition may inhibit the expression of DKK-1 protein in dermal papilla cells. Specifically, the composition may inhibit the expression of DKK-1 protein in dermal papilla cells where the expression of DKK-1 protein is induced by hormones such as DHT (dihydrotestosterone).

In a specific embodiment of the present invention, the composition containing the peptide of the present invention was treated at different concentrations to dermal papilla cell HHFDPC, which had been treated with DHT to induce the expression of DKK-1 protein. As a result of checking the composition for DKK-1 protein through Western blotting, it was confirmed that the amount of DKK-1 protein was reduced compared to the negative control group. Therefore, it was confirmed that the peptide of the present invention and the composition comprising the same are effective in suppressing the expression of hair loss-related proteins in dermal papilla cells and can be usefully used to prevent hair loss.

The composition may promote the expression of one or more selected from the group consisting of Ha3-II, Keratin 14, and Keratin 19 in outer root sheath cells. Specifically, the composition may increase the cellular activity of outer root sheath cells and promote the expression of Ha3-II, Keratin 14, and/or Keratin 19.

In a specific embodiment of the present invention, outer root sheath cell HHORSC were treated at different concentrations with the composition comprising the peptide of the present invention. As a result of confirming the expression of Ha3-II, Keratin 14, and Keratin 19 through RT-PCR, it was confirmed that the expression level was increased compared to the control group. Therefore, it was confirmed that the peptide of the present invention and the composition comprising the same have the effect of increasing the activity of outer root sheath cells, a type of cell that forms hair follicles, and thus have the effect of preventing hair loss or promoting hair growth.

The composition may promote the expression of MSX2 in germinal matrix cells. Specifically, the composition may induce the expression of genes related to the activity of germinal matrix cells by promoting the expression of MSX2, a transcription factor related to the cell activity of germinal matrix cells.

In a specific embodiment of the present invention, germinal matrix cell HHGMC were treated at different concentrations with the composition comprising the peptide of the present invention. As a result of confirming the expression of MSX2 through RT-PCR, it was confirmed that the expression level was increased compared to the control group. Therefore, it was confirmed that the peptide of the present invention and the composition comprising the same have the effect of increasing the activity of germinal matrix cells, a type of cell that forms hair, and thus have the effect of preventing hair loss or promoting hair growth.

2. Pharmaceutical Composition for Preventing or Treating Hair Loss

Another aspect of the present invention provides a pharmaceutical composition for preventing or treating hair loss comprising the peptide.

The peptide contains the amino acid sequence of SEQ ID NO: 1. The explanation for this is the same as the peptide described in the section 'Peptide having the activity of preventing hair loss or promoting hair growth and use thereof', and this is used for specific explanations. Hereinafter, only the components specific to the pharmaceutical composition will be explained.

As used herein, the term "prevention" means reducing the risk of developing a disease or disorder, and it refers to all actions that suppress or delay the onset of a disease by keeping it from progressing the development of one or more clinical symptoms of the disease in subjects who are easily exposed to or susceptible to the disease but do not yet have the disease or not show symptoms of the disease.

In the present invention, the term "treatment" means alleviating a disease or disorder, and includes all actions that improve or beneficially change the symptoms of a disease by arresting or reducing the progression of the disease or one or more clinical symptoms thereof.

In the pharmaceutical composition of the present invention, the peptide may be included in a therapeutically effective amount and may further include a pharmaceutically acceptable carrier. The term "therapeutically effective amount" refers to an amount sufficient to achieve the purpose of the present composition, prevention or treatment of hair loss.

In the present invention, hair loss means the absence of hair in areas where hair should normally exist, and includes a phenomenon in which the number of hairs decreases compared to the normal state. The hair loss is a concept that includes both non-cicatrical alopecia or cicatrical alopecia depending on whether the hair follicle is destroyed, for example, hereditary androgenetic alopecia, alopecia areata, tinea capitis due to fungal infection, telogen alopecia, trichotillomania, hair loss due to hair growth disorder disease or lupus, folliculitis decalvans, lichen planus pilaris, hair loss due to burns and/or trauma.

The prevention or treatment of hair loss may include removing the cause of hair loss or suppressing the progression of hair loss, and promoting hair growth by suppressing hair loss or promoting hair formation.

Meanwhile, the pharmaceutical composition of the present invention can be manufactured in unit dosage form by formulating using a pharmaceutically acceptable carrier and/or excipient, or can be manufactured by placing it in a multi-dose container, according to a method that can be easily performed by a person skilled in the art to which the present invention pertains. At this time, the formulation may be in the form of a solution in an oil or aqueous medium, suspension or emulsion, or may be in the form of an extract, powder, granule, tablet, capsule or gel (e.g., hydrogel), and may additionally contain a dispersant or stabilizer.

Additionally, the peptide included in the pharmaceutical composition may be transported in a pharmaceutically acceptable carrier such as colloidal suspension, powder, saline solution, lipid, liposome, microsphere, or nanospherical particle. It may form a complex or be associated with a delivery vehicle and can be transported in vivo using delivery systems known in the art, such as lipids, liposomes, microparticles, gold, nanoparticles, polymers, condensation agents, polysaccharides, polyamino acids, dendrimers, saponins, adsorption enhancers or fatty acids.

In addition, a pharmaceutically acceptable carrier may include, but is not limited to, lactose, dextrose, sucrose, sorbitol, mannitol, starch, gum acacia, calcium phosphate, alginate, gelatin, calcium silicate, microcrystalline cellulose, polyvinyl pyrolidone, cellulose, water, syrup, methyl cellulose, methyl hydroxy benzoate, propyl hydroxybenzoate, talc, magnesium stearate and mineral oil commonly used in preparation. In addition, in addition to the above ingredients, lubricants, wetting agents, sweeteners, flavoring agents, emulsifiers, suspending agents, preservatives, etc. may be additionally included.

The pharmaceutical composition according to the present invention can be administered orally or parenterally during clinical administration and can be used in the form of a general pharmaceutical preparation. That is, the pharmaceutical composition of the present invention can be administered in various oral and parenteral dosage forms during actual clinical administration. When formulated, it is prepared using diluents or excipients such as commonly used fillers, extenders, binders, wetting agents, disintegrants, and surfactants. Solid preparations for oral administration include tablets, pills, powders, granules, capsules, etc., and these solid preparations are prepared by mixing herbal extract or fermented herbal medicine with at least one excipients, such as starch, calcium carbonate, sucrose or lactose, and gelatin. Additionally, in addition to simple excipients, lubricants such as magnesium stearate, talc are also used. Liquid preparations for oral administration include suspensions, oral solutions, emulsions, and syrups. In addition to the commonly used simple diluents such as water and liquid paraffin, various excipients such as wetting agents, sweeteners, fragrances, and preservatives may be included. Preparations for parenteral administration include sterilized aqueous solutions, non-aqueous solutions, suspensions, emulsions, freeze-dried preparations, and suppositories. Non-aqueous solvents and suspensions may include propylene glycol, polyethylene glycol, vegetable oil such as olive oil, and injectable ester such as ethyl oleate. As a base for suppositories, wethepsol, macrogol, Tween 61, cacao, laurel, glycerol, gelatin, etc. can be used.

The dosage of the peptide may vary depending on factors such as formulation method, administration method, patient's age, weight, sex, pathological condition, food, administration time, administration route, excretion rate, and reaction sensitivity. It is generally 1 to 20 mg/day per 1 kg of body weight of an adult patient, preferably 5 to 10 mg/day, and may be administered in divided doses several times a day, preferably 2 to 3 times a day, at regular time intervals according to the judgment of a doctor or pharmacist.

The pharmaceutical composition of the present invention may be an external skin preparation. The external skin preparation is a preparation that can be used by applying it to the outside of the skin. When the pharmaceutical composition of the present invention is used as an external skin agent, it may be applied to the scalp, specifically the scalp in areas where hair loss has occurred or the scalp in areas where hair growth is to be promoted. The external skin preparation may be a cream, gel, ointment, skin emulsion, dermal suspension, transdermal patch, drug-impregnated bandage, lotion, or a combination thereof. The external skin preparation may be appropriately mixed with ingredients commonly used in external skin preparation such as cosmetics or pharmaceuticals, for example, water-based ingredients, oil-based ingredients, powder ingredients, alcohol, moisturizer, thickening agent, UV absorber, whitening agent, preservative, antioxidant, surfactant, fragrance, colorant, various skin nutrients, or combinations thereof, depending on need. In addition, metal chelating agents such as disodium edetate, trisodium edetate, sodium citrate, sodium polyphosphate, sodium metaphosphate or gluconic acid, drugs such as caffeine, tannin, verapamil, licorice extract, glabridin, hot water extracts of calin fruit, various herbal medicines, tocopherol acetate, glycyrrhizic acid, tranexamic acid and derivatives or salts thereof, vitamin C, magnesium ascorbyl phosphate, ascorbyl glucoside, albutin, kojic acid, and sugars such as glucose, fructose or trehalose can also be suitably incorporated in the external skin preparation.

3. Cosmetic Composition for Preventing or Improving Hair Loss

Another aspect of the present invention provides a cosmetic composition containing the peptide for preventing or improving hair loss.

The peptide contains the amino acid sequence of SEQ ID NO: 1. The explanation for this is the same as the peptide described in the section 'Peptide having the activity of preventing hair loss or promoting hair growth and use thereof', and this is used for specific explanations. Hereinafter, only the components specific to the cosmetic composition will be explained.

In the present invention, the term "improvement" refers to any action that improves or benefits the symptoms of a disease or disorder.

The prevention or improvement of hair loss may be removing the cause of hair loss or suppressing the progression of hair loss, or may be promoting hair growth by suppressing hair loss or promoting hair formation.

The cosmetic composition may include a cosmetically effective amount of the peptide and a cosmetically acceptable carrier, and the cosmetically effective amount refers to an amount sufficient to achieve the aforementioned hair loss prevention or hair growth promotion effect.

The cosmetic composition of the present invention may additionally contain, for example, other ingredients that have a synergistic effect on the activity of the peptide within a range that does not affect the hair loss prevention or hair growth promotion activity of the peptide. For example, it may contain adjuvants typically used in the cosmetic or dermatological fields, such as fat matters, organic solvents, solubilizers, concentrating agents, gelating agents, softening agents, antioxidants, suspending agents, stabilizers, foaming agents, fragrance, surfactants, water, ionic or nonionic emulsifying agents, fillers, sequestering agents, chelating agents, preservatives, vitamins, blocking agents, wetting agents, essential oils, dyes, pigments, hydrophilic or hydrophobic activators, lipid vesicles, or other ingredients typically used in cosmetics. The adjuvants may be used in an amount typically acceptable in the cosmetic or dermatological fields.

The cosmetic composition of the present invention can be prepared in any formulation commonly prepared in the art. For example, it can be formulated into a cosmetic product such as a solution, suspension, emulsion, gel, lotion, essence, cream, powder, soap, shampoo, conditioner, pack mask, surfactant-containing cleansing, cleansing foam, cleansing water, oil, liquid foundation, cream foundation, or spray.

When the formulation is a solution or emulsion, as a carrier component, a solvent, a solubilizer, or an emulsifier may be used. For example, water, ethanol, isopropanol, ethyl carbonate, ethyl acetate, benzyl alcohol, benzyl benzoate, propylene glycol, 1,3-butylglycol oil, glycerol aliphatic ester, polyethylene glycol or fatty acid ester of sorbitan may be used. When the formulation is a suspension, as a carrier component, a liquid diluent (e.g., water, ethanol, and propylene glycol), a suspending agent (e.g., ethoxylated isostearyl alcohol, polyoxyethylene sorbitol ester, and polyoxyethylene sorbitan ester), aluminum metahydroxide, microcrystalline cellulose, bentonite, agar, tragacanth, etc. may be used. When the formulation is cream or gel, as a carrier component, wax, paraffin, tragacanth, animal oil, starch, cellulose derivatives, silicone, bentonite, polyethylene glycol, silica, zinc oxide or talc may be used. When the formulation is powder or a spray, as a carrier component, silica, talc, aluminum hydroxide, lactose, calcium silicate, a propellant such as chlorofluorohydrocarbon, propane/butane, and dimethyl ether may be additionally contained. When the formulation is a surfactant-containing cleansing, as a carrier component, aliphatic alcohol sulfate, aliphatic alcohol ether sulfate, sulfosuccinic acid monoester, imidazolinium derivative, isethionate, methyltaurate, sarcosinate, fatty acid amide ether sulfate, aliphatic alcohol, alkylamidobetaine, fatty acid glyceride, fatty acid diethanolamide, vegetable oils, lanolin derivatives or ethoxylated glycerol fatty acid esters and the like may be used.

Specifically, the cosmetic composition of the present invention may be an external skin preparation. The external skin preparation is a preparation that can be used by applying it to the outside of the skin. When the cosmetic composition of the present invention is used as an external skin agent, it may be applied to the scalp, specifically the scalp in areas where hair loss has occurred or the scalp in areas where hair growth is to be promoted. The external skin preparation may be a cream, gel, ointment, skin emulsion, dermal suspension, transdermal patch, drug-impregnated bandage, lotion, or a combination thereof. The external skin preparation may be appropriately mixed with ingredients commonly used in external skin preparation such as cosmetics or pharmaceuticals, for example, water-based ingredients, oil-based ingredients, powder ingredients, alcohol, moisturizer, thickening agent, UV absorber, whitening agent, preservative, antioxidant, surfactant, fragrance, colorant, various skin nutrients, or combinations thereof, depending on need. In addition, metal chelating agents such as disodium edetate, trisodium edetate, sodium citrate, sodium polyphosphate, sodium metaphosphate or gluconic acid, drugs such as caffeine, tannin, verapamil, licorice extract, glabridin, hot water extracts of calin fruit, various herbal medicines, tocopherol acetate, glycyrrhizic acid, tranexamic acid and derivatives or salts thereof, vitamin C, magnesium ascorbyl phosphate, ascorbyl glucoside, albutin, kojic acid, and sugars such as glucose, fructose or trehalose can also be suitably incorporated in the external skin preparation.

Another aspect of the present invention provides a method of treating hair loss comprising administering a therapeutically effective amount of the peptide to a subject in need of treatment for hair loss.

Another aspect of the present invention provides a method for improving hair loss comprising administering a cosmetically effective amount of the peptide to a subject in need of improvement of hair loss.

In another aspect of the present invention, the use of the peptide for the treatment of alopecia is provided.

In another aspect of the present invention, the use of the peptide in the manufacture of a medicine for treating or preventing hair loss is provided.

Advantageous Effects

The peptide provided in the present invention has the activity of promoting the proliferation or activity of cells forming hair follicles or related to hair formation, such as dermal papilla cells, outer root sheath cells, and germinal matrix cells.

Specifically, the peptide of the present invention can increase the expression level of genes or proteins related to proliferation, differentiation, and activation of the cells, and has the activity of suppressing the expression of hair loss-related proteins induced by hormones such as DHT. Therefore, the peptide and the composition comprising the same can be usefully used to prevent, treat, or improve hair loss or to promote hair growth.

In addition, the peptide of the present invention and the composition comprising the same uses a single peptide as an active ingredient. Therefore, compared to hair loss improvement agents using natural products, which may contain a variety of ingredients and thus exhibit unpredictable effects, the peptide of the present invention and the composition comprising the same has the advantage of showing a local hair loss inhibition effect and then being easily decomposed and removed by proteolytic enzymes in the body, and because the mechanism of action is clearer, there is little or no possibility of side effects occurring. In addition, the composition of the present invention, which uses peptide as an active ingredient, has higher biocompatibility than existing therapeutic agents in that it uses a substance composed of amino acid bonds as an active ingredient. In addition, the composition has the advantage that the peptide may exhibit similar activity by mimicking the active site of a protein in the human body, and has the effect of reducing problems such as a decrease in sexual function due to hormonal regulation.

However, the effects of the present invention are not limited to the effects mentioned above, and other effects not mentioned will be clearly understood by those skilled in the art from the following description.

BEST MODE

Mode for Carrying Out the Invention

Hereinafter, the present invention will be described in detail through examples.

However, the following examples specifically illustrate the present invention, and the content of the present invention is not limited by the following examples.

EXAMPLE

[Preparation Example] Preparation of Peptide

A peptide having the amino acid sequence of SEQ ID NO: 1 listed in Table 1 below was synthesized using an automatic peptide synthesizer (Milligen 9050, Millipore, USA), and the synthesized peptide was purified using C18 reverse-phase high-performance liquid chromatography (HPLC) (Waters Associates, USA). The column used was ACQUITY UPLC BEH300 C18 (2.1 mm×100 mm, 1.7 μm, Waters Co, USA).

TABLE 1

| SEQ ID NO | Peptide sequence |
|---|---|
| 1 | QHNQIRYFEE |

[Experiment Example 1] Confirmation of the Effect of the Peptide of the Present Invention on Promoting Proliferation and Activity of Dermal Papilla Cells Using the peptide of the present invention consisting of the amino acid sequence of SEQ ID NO: 1 prepared according to the Preparation Example above, the proliferation-promoting and activity-promoting effects on dermal papilla cells, one of the cells forming hair follicles, were confirmed, and the inhibitory effect on hair loss-related proteins was confirmed.

[1-1] Confirmation of the Effect of Promoting Proliferation of Dermal Papilla Cells While culturing human hair follicle dermal papilla cells (HHFDPC), the absorbance was measured after treatment with the peptide of the present invention to confirm whether there was an effect of promoting the proliferation of the HHFDPC dermal papilla cells.

Specifically, HHFDPC (Sciencell, USA) was seeded at $4\times10^3$ cells/well in a 96-well culture plate, cultured in MSC complete medium (mesenchymal stem cell complete media, Sciencell, USA) for 24 hours, and then the medium was replaced with serum free MSC complete medium and cultured for another 24 hours. Then, the HHFDPC was treated with the peptide of SEQ ID NO: 1 prepared in the Preparation Example at concentrations of 500 nM, 5 μM, and 50 μM, respectively, and cultured at 37° C. for 72 hours. As a positive control, minoxidil was treated at a concentration of 1 μM, and as a negative control, HHFDPC without any treatment was used. Then, 10 μℓ of 5 mg/mL MTT solution was added and cultured in a 37° C. $CO_2$ incubator for 4 hours to stain the cells. After removing the medium, the cells were treated with 100 μl of DMSO and shaken for 10 minutes, and the number of HHFDPC cells was confirmed by measuring absorbance at a wavelength of 540 nm using a spectrophotometer.

Figure 1:
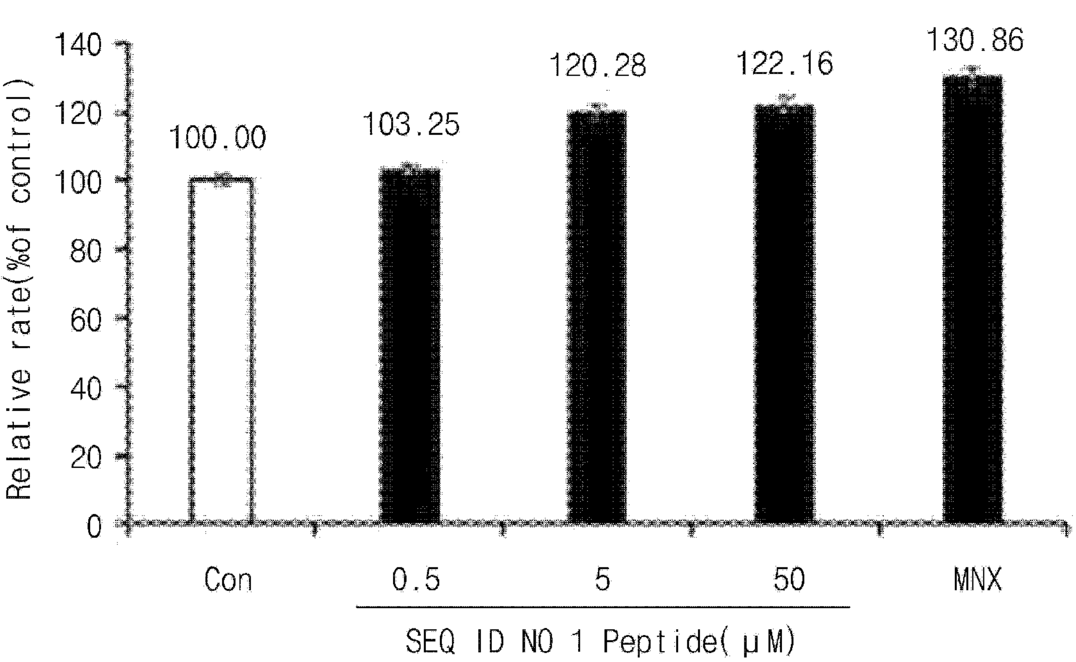
FIG. 1 is a graph showing the results of comparing cell proliferation with the values of the untreated control group (Con) and the minoxidil-treated positive control group (MNX) after treating HHFDPC with the peptide containing the amino acid sequence of SEQ ID NO: 1 of the present invention at various concentrations.

As a result, as can be seen in FIG. 1, the absorbance was measured to be higher in the group treated with the peptide of the present invention compared to the untreated control group, confirming that the proliferation of HHFDPC was promoted depending on the concentration of the treated peptide and the number of cells increased further. Through the above results, it was confirmed that the peptide of the present invention has the effect of increasing the number of dermal papilla cells, and dermal papilla cells correspond to cells that form hair follicles that produce hair, and are effective in promoting hair growth and improving hair loss.

[1-2] Confirmation of Increased Effect of Factors Related to Proliferation of Dermal Papilla Cells In the HHFDPC treated with the peptide of the present invention, changes in related factors that affect cell proliferation or differentiation were confirmed to determine whether the peptide of the present invention could promote proliferation and differentiation of HHFDPC by increasing them.

First, phosphorylated forms of AKT and ERK, which act as signaling molecules related to the proliferation of HHFDPC, were confirmed through Western blotting. Specifically, HHFDPC as in [Experiment Example 1-1] above was seeded at $4\times10^5$ cells/well in a 6-well culture plate, cultured in MSC complete medium (mesenchymal stem cell complete media) for 24 hours, and then the medium was replaced with serum free MSC complete medium and cultured for another 24 hours. Then, the HHFDPC was treated with the peptide of SEQ ID NO: 1 prepared in the Preparation Example at concentrations of 500 nM, 5 μM, and 50 μM, respectively, and cultured at 37° C. for 24 hours. As a positive control, minoxidil was treated at a concentration of 1 μM, and as a negative control, HHFDPC without any treatment was used. Then, Western blotting was performed to detect phosphorylated AKT and phosphorylated ERK. After washing with PBS, the cells were treated with 100 μℓ of lysis buffer to destroy cells, thereby obtaining cell lysate. After electrophoresis using a 10% SDS-PAGE gel, it was transferred to a PVDF membrane and blocked using 5% skim milk at room temperature for 30 minutes. And, to detect phosphorylated AKT (p-AKT) and phosphorylated ERK (p-ERK), anti-p-AKT antibody and anti-p-ERK antibody (cell signaling, USA) capable of specifically binding to p-AKT and p-ERK, respectively, were diluted 1:1000 in 3% BSA and reacted with the PVDF membrane at 4° C. for 16 hours. Afterwards, washed three times for 15 minutes each with 0.1% PBS-T (0.1% Tween-20 in PBS), secondary antibodies against the above antibodies were diluted 1:2000 in 5% skim milk and reacted at room temperature for 1 hour. After washing again with 0.1% PBS-T (0.1% Tween-20 in PBS) three times for 15 minutes each, p-AKT and p-ERK were detected by treatment with ECL solution (GE Healthcare, USA).

Figure 2:
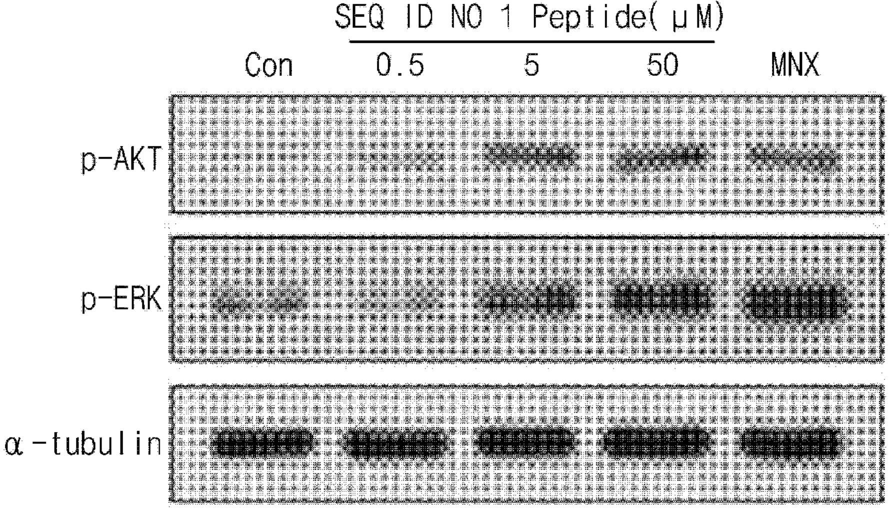
FIG. 2 is the results of confirming phosphorylated AKT and ERK (p-AKT and p-ERK, respectively) through Western blotting in the group treated with the peptide containing the amino acid sequence of SEQ ID NO: 1 of the present invention at different concentrations in HHFDPC, the control group without any treatment (Con), and the positive control group treated with minoxidil (MNX).

As a result, as can be seen in FIG. 2, p-AKT and p-ERK, signaling molecules related to proliferation, were detected in HHFDPC treated with the peptide of the present invention, and phosphorylation was found to be increased compared to the control group not treated with the peptide. Based on the above results, it was confirmed that the peptide of the present invention has the effect of activating signals related to the proliferation of dermal papilla cells forming hair follicles, thereby promoting the proliferation of dermal papilla cells and promoting hair growth.

In addition, in addition to p-AKT and p-ERK, in order to confirm the activation of β-catenin, which is known to affect cell proliferation and differentiation, whether β-catenin moved into the nucleus was confirmed through Western blotting. Specifically, the HHFDPC as in [Experiment Example 1-1] was seeded in a 6-well culture plate at an amount of $4\times10^5$ cells/well, cultured in MSC complete medium (mesenchymal stem cell complete media) for 24 hours. Next, the medium was replaced with serum free MSC complete medium and cultured again for 24 hours. Then, the HHFDPC was treated with the peptide of SEQ ID NO: 1 prepared in the Preparation Example at concentrations of 500 nM, 5 μM, and 50 μM, respectively, and cultured at 37° C. for 24 hours. As a positive control, minoxidil was treated at a concentration of 1 μM, and as a negative control, HHFDPC without any treatment was used. After washing with PBS, proteins in the nucleus were isolated using a nuclear protein extraction kit (Thermo scientific, USA). After electrophoresis using a 10% SDS-PAGE gel, it was transferred to a PVDF membrane and blocked using 5% skim milk at room temperature for 30 minutes. To detect β-catenin, anti-β-catenin (cell signaling, USA), which can specifically bind to β-catenin, was diluted 1:1000 in 3% BSA and reacted with the PVDF membrane at 4° C. for 16 hours. Afterwards, washed three times for 15 minutes each with 0.1% PBS-T (0.1% Tween-20 in PBS), secondary antibodies against the above antibodies were diluted 1:2000 in 5% skim milk and reacted at room temperature for 1 hour. After washing again with 0.1% PBS-T (0.1% Tween-20 in PBS) three times for 15 minutes each, β-catenin was detected by treatment with ECL solution (GE Healthcare, USA).

Figure 3:
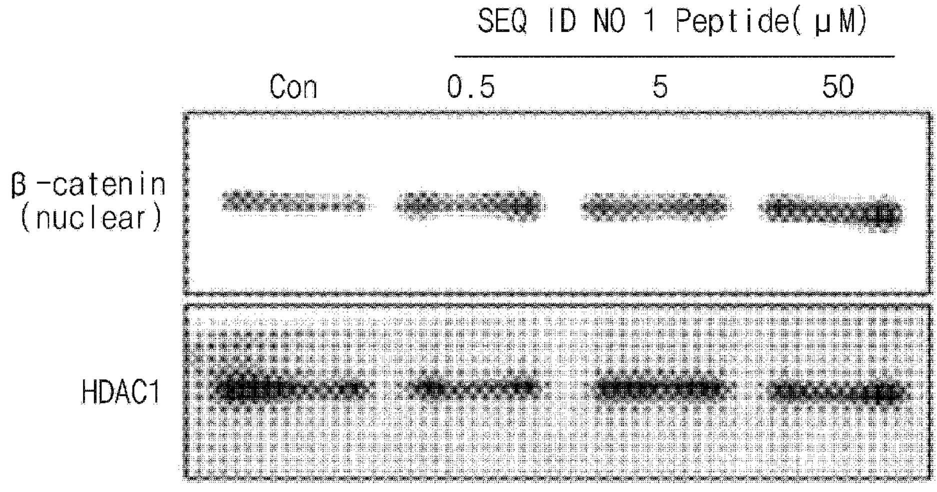
FIG. 3 is the result of confirming β-catenin moved to the nucleus through Western blotting in the group treated with the peptide containing the amino acid sequence of SEQ ID NO: 1 of the present invention at different concentrations in HHFDPC and the control group without any treatment (Con).

As a result, as can be seen in FIG. 3, R-catenin was found to be moved and present in the nucleus of HHFDPC treated with the peptide of the present invention. Additionally, compared to the control group that was not treated with the peptide, it was confirmed that migration due to activation of β-catenin increased and that the activation of β-catenin was further promoted depending on the concentration of the peptide of the present invention.

Furthermore, in order to determine whether the β-catenin moves to the nucleus and is activated to affect proliferation and differentiation, whether the expression of LEF-1, c-Myc and cyclin D1 (cyclin D1), which act as downstream factors, increases with β-catenin activation was confirmed through RT-PCR. Specifically, in the same manner as the previous Western blotting experiment, HHFDPC cells were cultured, treated with the peptides of the Preparation Example of the present invention at concentrations of 500 nM, 5 μM, and 50 μM, respectively, and cultured at 37° C. for 24 hours. After washing the cells with PBS, RNA was isolated by treating them with 300 μℓ of easy blue (intron, Korea). Then, cDNA was synthesized using a cDNA synthesis kit (enzynomics, Korea) by quantifying it with nano drop, and PCR was performed using primers for LEF-1, c-Myc and cyclin D1 (base sequences of the primer are listed in Table 2 below) and PCR premix (enzynomics, Korea). Electrophoresis was performed on a 1.5% agarose gel, and then the mRNA of LEF-1, c-Myc, c-Myc and cyclin D1 was detected using a band analysis system (Bio-Rad gel image system).

TABLE 2

| SEQ ID NO | Sequence name | Base sequence |
|---|---|---|
| 2 | LEF-1 Forward primer | (5') CCAGCTATTGTAACACCTCA (3') |
| 3 | LEF-1 Reverse primer | (5') TTCAGATGTAGGCAGCTGTC (3') |
| 4 | c-Myc Forward primer | (5') ACCAGCAGCGACTCTGAGGAGGAAC (3') |
| 5 | c-Myc Reverse primer | (5') TGACCCTCTTGGCAGCAGGATAGTCC (3') |
| 6 | cyclin-D1 Forward primer | (5') ACCTTCGTTGCCCTCTGTGCCACAGATG (3') |
| 7 | cyclin-D1 Reverse primer | (5') AGGCCCGGAGGCAGTCCGGGT (3') |
| 8 | GAPDH Forward primer | (5') GGAGCCAAAAGGGTCATCAT (3') |
| 9 | GAPDH Reverse primer | (5') GTGATGGCATGGACTGTGGT (3') |

Figure 4:
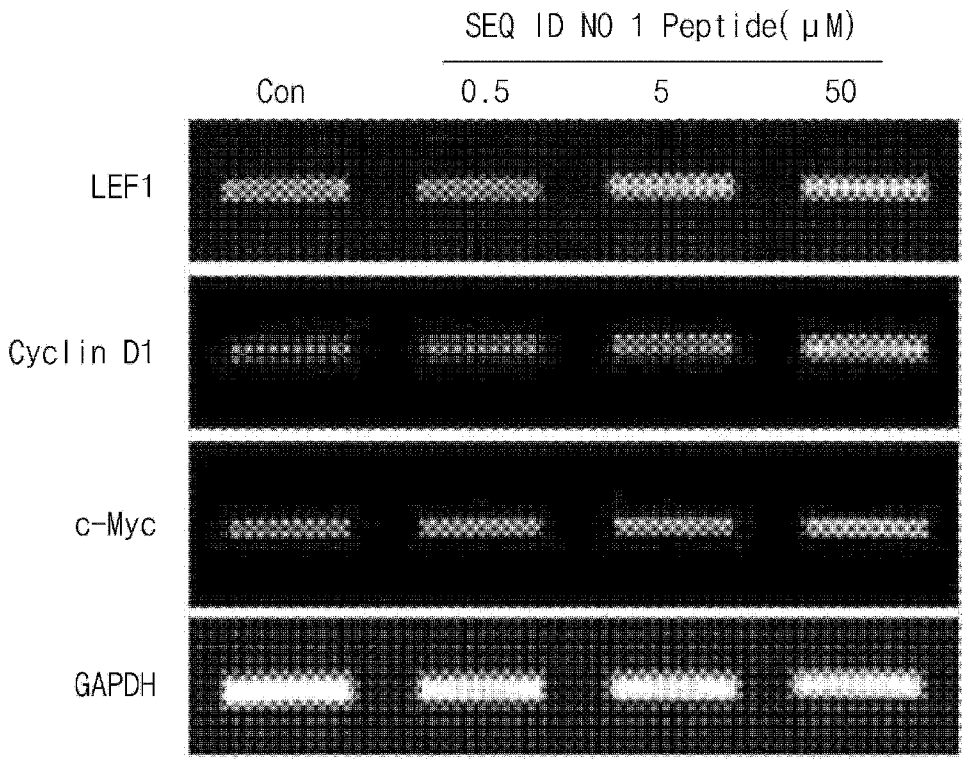
FIG. 4 is the result of confirming the expression of LEF-1, c-Myc and cyclin D1 through RT-PCR in the group treated with the peptide containing the amino acid sequence of SEQ ID NO: 1 of the present invention at different concentrations in HHFDPC and the control group without any treatment (Con).

As a result, as can be seen in FIG. 4, mRNA of LEF-1, c-Myc and cyclin D1 was detected in HHFDPC treated with the peptide of the present invention, and the amount of mRNA increased further compared to the control group without any treatment. Therefore, it was confirmed that in dermal papilla cells treated with the peptide of the present invention, the expression of LEF-1, c-Myc and cyclin D1, which are expressed as β-catenin is activated, is promoted, and the proliferation and differentiation of dermal papilla cells are promoted, thereby promoting hair formation.

[Experiment Example 2] Confirmation of the Inhibitory Effect of the Peptide of the Present Invention on the Expression of Hair Loss-Related Proteins in Dermal Papilla Cells DKK-1 protein (dickkopf-related protein 1) is a hair loss-related protein known to be highly expressed in individuals with hair loss, especially male pattern hair loss, and its expression is known to be promoted by hormones such as DHT (Dihydrotestosterone). Accordingly, the expression of DKK-1 protein was induced by treating HHFDPC cells with DHT together with the peptide according to the Preparation Example of the present invention, and then the expression level of DKK-1 was measured through Western blotting to determine whether there was an effect of suppressing the expression of DKK-1 protein.

Specifically, HHFDPC as in [Experiment Example 1-1] was seeded in a 6-well culture plate at $4\times10^5$ cells/well and then cultured in MSC complete medium (mesenchymal stem cell complete media) for 24 hours. Next, the medium was replaced with serum free MSC complete medium and cultured again for 24 hours. In addition, the HHFDPC was treated with the peptide of SEQ ID NO: 1 prepared in the Preparation Example at concentrations of 500 nM, 5 μM, and 50 μM, respectively, and at this time, DHT, an expression inducer of DKK-1 protein, was simultaneously treated at a concentration of 100 nM and then cultured at 37° C. for 24 hours. As a positive control, HHFDPC treated with finasteride at a concentration of 5 μM was used, and as a negative control, HHFDPC treated with only DHT to induce DKK-1 expression and not treated with peptide was used. Then, Western blotting was performed to detect DKK-1 protein, a hair loss-related protein. After washing with PBS, the cells were treated with lysis buffer to destroy cells, thereby obtaining cell lysate. After electrophoresis using a 10% SDS-PAGE gel, it was transferred to a PVDF membrane and blocked using 5% skim milk at room temperature for 30 minutes. And, to detect DDK-1 protein, DKK-1 antibody (cell signaling, USA) capable of specifically binding thereto was diluted 1:1000 in 3% BSA and reacted with the PVDF membrane for 16 hours at 4° C. Afterwards, washed three times for 15 minutes each with 0.1% PBS-T (0.1% Tween-20 in PBS), secondary antibody against the anti-DKK-1 antibody was diluted 1:2000 in 5% skim milk and reacted at room temperature for 1 hour. After washing again with 0.1% PBS-T (0.1% Tween-20 in PBS) three times for 15 minutes each, DKK-1 protein was detected by treatment with ECL solution (GE Healthcare, USA).

Figure 5:
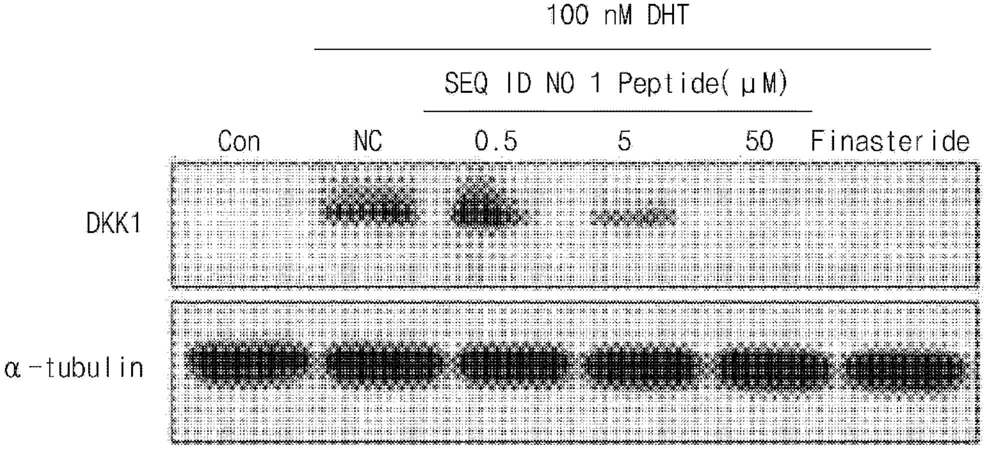
FIG. 5 is the result of confirming the DKK-1 protein through Western blotting in the group treated with the peptide containing the amino acid sequence of SEQ ID NO: 1 of the present invention at different concentrations in DHT-treated HHFDPC, the control group without any treatment (Con), and the positive control group treated with finasteride (Finasteride).

As a result, as can be seen in FIG. 5, the amount of DKK-1 protein was found to be reduced in HHFDPC treated with the peptide of the present invention compared to the negative control group. In other words, treatment of dermal papilla cells with DHT increased the expression of a hair loss-related protein (negative control). However, when treated with the peptide of the present invention, the amount of DKK-1 protein increased by the treatment of DHT decreased again in HHFDPC, and the increased expression of DKK-1 decreased again depending on the concentration of the peptide of the present invention. Therefore, it was confirmed that the peptide of the present invention has the effect of suppressing hair loss.

[Experiment Example 3] Confirmation of the Effect of the Peptide of the Present Invention on Promoting Outer Root Sheath Cell Activity Using the peptide of the present invention consisting of the amino acid sequence of SEQ ID NO: 1 prepared according to Preparation Example above, it was confirmed whether it promotes the activity of outer root sheath cells, a type of cell that forms hair follicles.

Specifically, HHORSC (human hair outer root sheath cell, Sciencell, USA) was seeded in a 6-well culture plate at $4\times10^5$ cells/well and then cultured in MSC complete medium (mesenchymal stem cell complete media) for 24 hours. Next, the medium was replaced with serum free MSC complete medium and cultured again for 24 hours. Then, the HHORSC was treated with the peptide of SEQ ID NO: 1 prepared in the Preparation Example at concentrations of 500 nM, 5 μM, and 50 μM, respectively, and cultured at 37° C. for 72 hours. As a positive control, EGF was treated at a concentration of 50 nM, and as a negative control, HHORSC without any treatment was used. After washing with PBS, RNA was isolated by treating with 300 μℓ of easy blue (intron, Korea). Then, cDNA was synthesized using a cDNA synthesis kit (enzynomics, Korea) by quantification using nano drop, and PCR was performed using primers for Ha3-II, Keratin 14, and Keratin 19 (base sequences of primer are listed in Table 3 below) and PCR premix (enzynomics, Korea). Electrophoresis was performed on a 1.5% agarose gel, and the mRNAs of Ha3-II, Keratin 14, and Keratin 19 were detected using a band analysis system (Bio-Rad gel image system).

TABLE 3

| SEQ ID NO | Sequence name | Base sequence |
|---|---|---|
| 10 | Ha3-II Forward primer | (5') GATCATCGAGCTGAGACGCA (3') |
| 11 | Ha3-II Reverse primer | (5') CTGGCCCCAGGGTATCTAGT (3') |
| 12 | Keratin 14 Forward primer | (5') CCAAATCCGCACCAAGGTCA (3') |
| 13 | Keratin 14 Reverse primer | (5') GTATTGATTGCCAGGAGGGGG (3') |
| 14 | Keratin 19 Forward primer | (5') CGCGGCGTATCCGTGTCCTC (3') |
| 15 | Keratin 19 Reverse primer | (5') AGCCTGTTCCGTCTCAAACTTGGT (3') |

Figure 6:
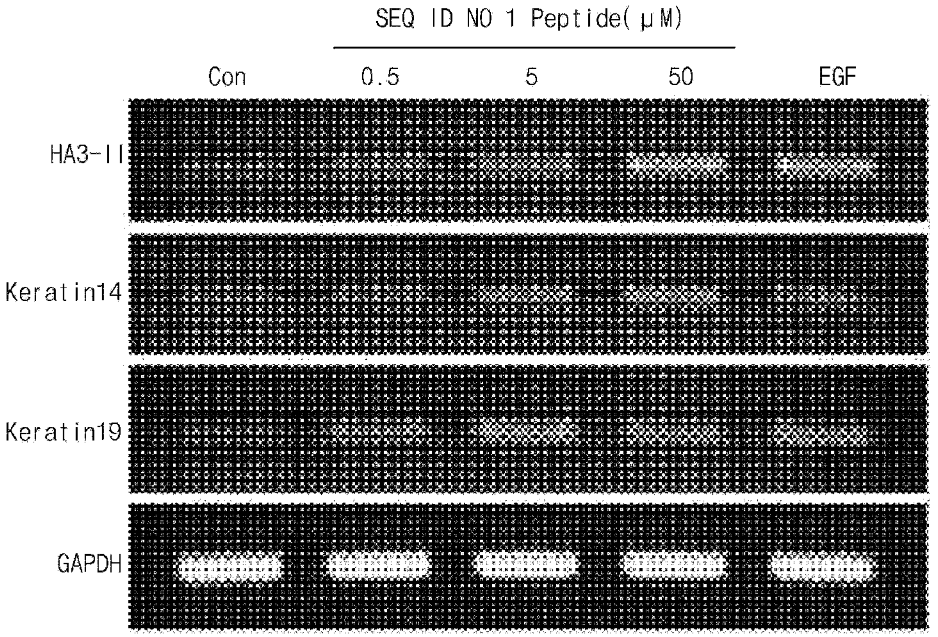
FIG. 6 is the result of confirming the expression of Ha3-II, Keratin 14, and Keratin 19 through RT-PCR in the group treated with the peptide containing the amino acid sequence of SEQ ID NO: 1 of the present invention at different concentrations in HHORSC, the control group without any treatment (Con), and the positive control group treated with EGF.

As a result, as can be seen in FIG. 6, mRNA of Ha3-II, Keratin 14, and Keratin 19 was detected in HHORSC treated with the peptide of the present invention, and the amount of mRNA increased further compared to the control group that did not receive any treatment. Therefore, it was confirmed that the expression of the above-mentioned cytokines increased in outer root sheath cells treated with the peptide of the present invention as their cellular activity increased. In addition, it was confirmed that the peptide of the present invention has the effect of increasing the activity of outer root sheath cells, which form hair follicles and help form hair.

[Experiment Example 4] Confirmation of the Effect of the Peptide of the Present Invention on Promoting Germinal Matrix Cell Activity Using the peptide of the present invention consisting of the amino acid sequence of SEQ ID NO: 1 prepared according to Preparation Example above, it was confirmed whether it promoted the expression of transcription factors related to the activity of germinal matrix cells, a type of cell that forms hair.

Specifically, HHGMC (human hair germinal matrix cell, Sciencell, USA) was seeded in a 6-well culture plate at $4\times10^5$ cells/well and then cultured in MSC complete medium (mesenchymal stem cell complete media) for 24 hours. Next, the medium was replaced with serum free MSC complete medium and cultured again for 24 hours. Then, the HHGMC was treated with the peptide of SEQ ID NO: 1 prepared in the Preparation Example at concentrations of 500 nM, 5 μM, and 50 μM, respectively, and cultured at 37° C. for 72 hours. As a positive control, EGF was treated at a concentration of 50 nM, and as a negative control, HHGMC without any treatment was used. After washing with PBS, RNA was isolated by treating with 300 μℓ of easy blue (intron, Korea). Next, cDNA was synthesized using a cDNA synthesis kit (enzynomics, Korea) by quantification using nano drop, and PCR was performed using primers for MSX2 (base sequences of primer are listed in Table 4 below) and PCR premix (enzynomics, Korea). Electrophoresis was performed on a 1.5% agarose gel, and MSX2 mRNA was detected using a band analysis system (Bio-Rad gel image system).

TABLE 4

| SEQ ID NO | Sequence name | Base sequence |
|---|---|---|
| 16 | MSX2 Forward primer | (5') CGGTCAAGTCGGAAAATTCA (3') |
| 17 | MSX2 Reverse primer | (5') GAGGAGCTGGGATGTGGTAA (3') |

Figure 7:
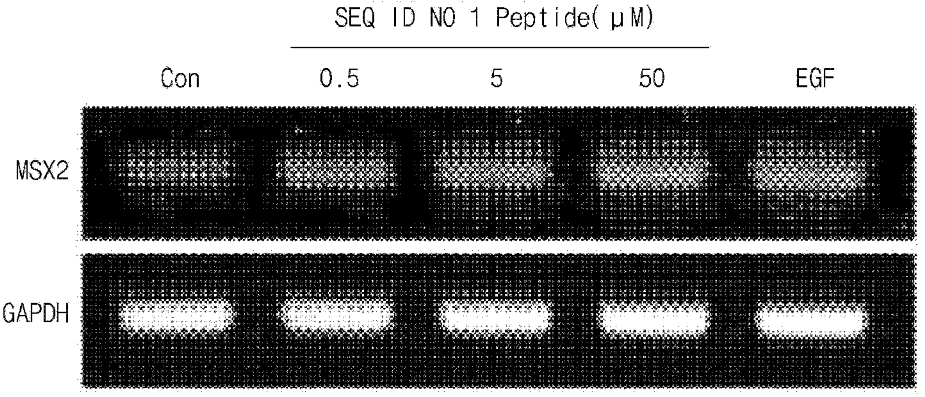
FIG. 7 is the result of confirming the expression of MSX2 through RT-PCR in the group treated with the peptide containing the amino acid sequence of SEQ ID NO: 1 of the present invention at various concentrations in HHGMC, the control group without any treatment (Con), and the positive control group treated with EGF.

As a result, as can be seen in FIG. 7, MSX2 mRNA was detected in the HHGMC treated with the peptide of the present invention, and the amount of mRNA increased further compared to the untreated control group. Therefore, it was confirmed that in the germinal matrix cells treated with the peptide of the present invention, the transcription and corresponding activity of genes related to cell activity increase as the expression of the transcription factor MSX2 increases, and the peptide of the present invention has the effect of promoting hair formation and preventing and improving hair loss by increasing the activity of germinal matrix cells.

In the above, the present invention has been described in detail only with respect to the described embodiments, but it is obvious to those skilled in the art that various changes and modifications are possible within the technical scope of the present invention, and it is natural that such changes and modifications fall within the scope of the appended claims.

The invention claimed is:

1. A peptide having the activity of preventing hair loss or promoting hair growth, comprising an amino acid sequence of SEQ ID NO: 1.

2. The peptide according to claim 1, wherein the peptide promotes the proliferation of dermal papilla cells.

3. A composition for preventing hair loss or promoting hair growth, comprising the peptide of claim 1.

4. The composition for preventing hair loss or promoting hair growth according to claim 3, wherein the peptide is included in the composition at a concentration of 0.01 μM to 100 μM.

5. The composition for preventing hair loss or promoting hair growth according to claim 3, , wherein the composition induces phosphorylation of AKT ERK, or both in dermal papilla cells.

6. The composition for preventing hair loss or promoting hair growth according to claim 3, wherein the composition induces the activation of B-catenin in dermal papilla cells.

7. The composition for preventing hair loss or promoting hair growth according to claim 3, wherein the composition promotes one or more expressions selected from the group consisting of LEF-1, c-Myc and cyclin D1 in dermal papilla cells.

8. The composition for preventing hair loss or promoting hair growth according to claim 3, wherein the composition inhibits the expression of DKK-1 protein in dermal papilla cells.

9. The composition for preventing hair loss or promoting hair growth according to claim 3, wherein the composition promotes one or more expressions selected from the group consisting of Ha3-II, Keratin 14 and Keratin 19 in outer root sheath cells.

10. The composition for preventing hair loss or promoting hair growth according to claim 3, wherein the composition promotes the expression of MSX2 in germinal matrix cells.

11. A pharmaceutical composition for preventing or treating hair loss, comprising the peptide of claim 1.

12. The pharmaceutical composition for preventing or treating hair loss according to claim 11, wherein the pharmaceutical composition is an external skin preparation.

13. A cosmetic composition for preventing or improving hair loss, comprising the peptide of claim 1.

14. The cosmetic composition for preventing or improving hair loss according to claim 13, wherein the cosmetic composition is an external skin preparation.

15. The cosmetic composition for preventing or improving hair loss according to claim 13, wherein the cosmetic composition is formulated as a formulation selected from the group consisting of solution, suspension, emulsion, gel, lotion, essence, cream, powder, soap, shampoo, conditioner, pack mask, surfactant-containing cleansing, cleansing foam, cleansing water, oil, liquid foundation, cream foundation and spray.

16. A method for preventing or treating hair loss in a subject in need thereof, the method comprising administering to the subject a therapeutically effective amount of the peptide of claim 1.

17. The method according to claim 16, wherein the peptide is administered in the form of a pharmaceutical composition.

18. A method for promoting hair growth in a subject in need thereof, the method comprising administering to the subject an amount of the peptide of claim 1 effective for promoting hair growth.

* * * * *

SEQUENCE LISTING

```
Sequence total quantity: 17
SEQ ID NO: 1            moltype = AA  length = 10
FEATURE                 Location/Qualifiers
source                  1..10
                        mol_type = protein
                        organism = synthetic construct
SEQUENCE: 1
QHNQIRYFEE                                                          10

SEQ ID NO: 2            moltype = DNA  length = 20
FEATURE                 Location/Qualifiers
source                  1..20
                        mol_type = other DNA
                        organism = synthetic construct
SEQUENCE: 2
ccagctattg taacacctca                                               20

SEQ ID NO: 3            moltype = DNA  length = 20
FEATURE                 Location/Qualifiers
source                  1..20
                        mol_type = other DNA
                        organism = synthetic construct
SEQUENCE: 3
ttcagatgta ggcagctgtc                                               20

SEQ ID NO: 4            moltype = DNA  length = 25
FEATURE                 Location/Qualifiers
source                  1..25
                        mol_type = other DNA
                        organism = synthetic construct
SEQUENCE: 4
accagcagcg actctgagga ggaac                                         25

SEQ ID NO: 5            moltype = DNA  length = 26
FEATURE                 Location/Qualifiers
```

```
source                  1..26
                        mol_type = other DNA
                        organism = synthetic construct
SEQUENCE: 5
tgaccctctt ggcagcagga tagtcc                                           26

SEQ ID NO: 6            moltype = DNA  length = 28
FEATURE                 Location/Qualifiers
source                  1..28
                        mol_type = other DNA
                        organism = synthetic construct
SEQUENCE: 6
accttcgttg ccctctgtgc cacagatg                                         28

SEQ ID NO: 7            moltype = DNA  length = 21
FEATURE                 Location/Qualifiers
source                  1..21
                        mol_type = other DNA
                        organism = synthetic construct
SEQUENCE: 7
aggcccggag gcagtccggg t                                                21

SEQ ID NO: 8            moltype = DNA  length = 20
FEATURE                 Location/Qualifiers
source                  1..20
                        mol_type = other DNA
                        organism = synthetic construct
SEQUENCE: 8
ggagccaaaa gggtcatcat                                                  20

SEQ ID NO: 9            moltype = DNA  length = 20
FEATURE                 Location/Qualifiers
source                  1..20
                        mol_type = other DNA
                        organism = synthetic construct
SEQUENCE: 9
gtgatggcat ggactgtggt                                                  20

SEQ ID NO: 10           moltype = DNA  length = 20
FEATURE                 Location/Qualifiers
source                  1..20
                        mol_type = other DNA
                        organism = synthetic construct
SEQUENCE: 10
gatcatcgag ctgagacgca                                                  20

SEQ ID NO: 11           moltype = DNA  length = 20
FEATURE                 Location/Qualifiers
source                  1..20
                        mol_type = other DNA
                        organism = synthetic construct
SEQUENCE: 11
ctggccccag ggtatctagt                                                  20

SEQ ID NO: 12           moltype = DNA  length = 20
FEATURE                 Location/Qualifiers
source                  1..20
                        mol_type = other DNA
                        organism = synthetic construct
SEQUENCE: 12
ccaaatccgc accaaggtca                                                  20

SEQ ID NO: 13           moltype = DNA  length = 21
FEATURE                 Location/Qualifiers
source                  1..21
                        mol_type = other DNA
                        organism = synthetic construct
SEQUENCE: 13
gtattgattg ccaggagggg g                                                21

SEQ ID NO: 14           moltype = DNA  length = 20
FEATURE                 Location/Qualifiers
source                  1..20
                        mol_type = other DNA
                        organism = synthetic construct
SEQUENCE: 14
cgcggcgtat ccgtgtcctc                                                  20

SEQ ID NO: 15           moltype = DNA  length = 24
```

-continued

```
FEATURE                 Location/Qualifiers
source                  1..24
                        mol_type = other DNA
                        organism = synthetic construct
SEQUENCE: 15
agcctgttcc gtctcaaact tggt                                            24

SEQ ID NO: 16           moltype = DNA  length = 20
FEATURE                 Location/Qualifiers
source                  1..20
                        mol_type = other DNA
                        organism = synthetic construct
SEQUENCE: 16
cggtcaagtc ggaaaattca                                                 20

SEQ ID NO: 17           moltype = DNA  length = 20
FEATURE                 Location/Qualifiers
source                  1..20
                        mol_type = other DNA
                        organism = synthetic construct
SEQUENCE: 17
gaggagctgg gatgtggtaa                                                 20
```